United States Patent [19]
Bae

[11] Patent Number: 5,905,017
[45] Date of Patent: *May 18, 1999

[54] METHOD FOR DETECTING MICROSCOPIC DIFFERENCES IN THICKNESS OF PHOTORESIST FILM COATED ON WAFER

[75] Inventor: Sang Man Bae, Kyoungki-do, Rep. of Korea

[73] Assignee: Hyundai Electronics Industries Co., Ltd., Kyoungki-do, Rep. of Korea

[*] Notice: This patent issued on a continued prosecution application filed under 37 CFR 1.53(d), and is subject to the twenty year patent term provisions of 35 U.S.C. 154(a)(2).

[21] Appl. No.: 08/839,201

[22] Filed: Apr. 23, 1997

Related U.S. Application Data

[63] Continuation of application No. 08/498,571, Jul. 6, 1995, abandoned.

[30] Foreign Application Priority Data

Jul. 11, 1994 [KR] Rep. of Korea ..................... 94-16656

[51] Int. Cl.[6] ...................................................... G03C 5/00
[52] U.S. Cl. ..................................... 430/272.1; 430/273.1; 430/30
[58] Field of Search .................................. 430/30, 272.1, 430/273.1, 327, 330, 315, 324

[56] References Cited

U.S. PATENT DOCUMENTS

| | | | |
|---|---|---|---|
| 4,774,164 | 9/1988 | Peavey et al. | 430/330 X |
| 4,824,763 | 4/1989 | Lee | 430/330 X |
| 5,023,203 | 6/1991 | Choi | 438/696 |
| 5,116,704 | 5/1992 | Kwon | 430/330 X |
| 5,153,103 | 10/1992 | Kotuchi et al. | 430/330 X |
| 5,326,675 | 7/1994 | Niki et al. | 430/330 X |
| 5,536,534 | 7/1996 | Bae | 427/375 |
| 5,593,813 | 1/1997 | Kim | 430/312 |

*Primary Examiner*—Bernard Codd
*Attorney, Agent, or Firm*—Nath & Associates; Gary M. Nath; Harold L. Novick

[57] ABSTRACT

A method for detecting microscopic differences in the thickness of a photoresist film coated on a wafer through naked eyes, which is capable of accurately controlling the critical dimension of the photoresist film patterns even in devices of 256 M DRAM or more and allows the yield to be analyzed with accuracy, comprising the steps of: subjecting the photoresist film to thermal treatment at a low temperature, to make some low molecular weight compounds or solvent molecules to remain within the photoresist film; forming a special material layer over the photoresist film within a certain thickness; and executing high-temperature thermal treatment, to gush up the remaining low-molecular weight compounds or solvent molecules from the photoresist film through relative thin parts of the special material layer.

8 Claims, 1 Drawing Sheet

METHOD FOR DETECTING MICROSCOPIC DIFFERENCES IN THICKNESS OF PHOTORESIST FILM COATED ON WAFER

This application is a continuation of U.S. patent application Ser. No. 08/498,571, filed Jul. 6, 1995, now abandoned, the contents of which are incorporated herein in their entirety.

BACKGROUND OF THE INVENTION

1. Field of the Invention

The present invention relates, in general, to a method for detecting microscopic differences in the thickness of a photoresist film coated on a wafer. More particularly, the present invention is concerned with a method for detecting the microscopic differences visibly such that the topology of the photoresist film can be improved easily.

2. Description of the Prior Art

As the design rule is smaller or the relative size of a wafer is smaller, which is attributed to the high integration of devices, it is more difficult to maintain uniformly the critical dimension (hereinafter referred to as "CD") of the patterns which are formed on many dies all over the wafer by lithography. In addition, microscopic differences in the thickness of the photoresist film coated on the wafer causes a difference in standing wave effect in spite of the same exposure energy, resulting in an alteration of the CD of each of the dies formed over the wafer. The amount of standing wave effect (S) is represented as Equation I:

$$S = C(R_1 \times R_2)^{1/2} e^{-\alpha D} \quad [I]$$

wherein C stands for constant;

$R_1$ and $R_2$ each are the intensity of a light scattered from the boundary between the bottom of a photoresist film and the upper surface of the wafer;

a is a light transmittivity parameter associated with the components of the photoresist film; and D is the thickness of the photoresist film.

Because the amount of standing wave effect (S) has a proportional relation as represented in Equation I, the change of S value arises dependently on the $R_1$ and $R_2$ values with the same period with the thickness in the photoresist film.

With reference to FIG. 1, there is shown a curve of CD with respect to thickness of a photoresist film coated on a wafer. As shown in this curve, CD values are periodically changed. The change of CD value is dependent on the values of $R_1$ and $R_2$. In the figure, reference character "t" is a coating thickness difference of photoresist film which corresponds to a period of the standing wave effect. The coating thickness difference of photoresist film is proportional to $\lambda/4n$ wherein $\lambda$ is a wavelength and n is a refractive index. Thus, the coating thickness difference of photoresist film (t) is microscopically change din a highly integrated device which has been exposed to a light source with a short wavelength, thereby changing the CD value. For 256 M DRAM (mega dynamic random access memory) an excimer laser having a wavelength of 248 nm is used for a photoresist film with a refractive index ranging from 1.6 to 1.7.

Generally speaking, spin-coat processes show their own characteristic differences in the coating thickness of photoresist film. The differences according to the spin-coat processes are unable to be measured by naked eyes. This is possible with a special measuring apparatus. However, there arise problems when measuring the coating state by means of such apparatus. Because measurements at many locations of the coating, which may be necessary for the accurate examination into the coating state of photoresist film, cannot be carried out or recognition of the outline of the coating shape is not possible, it is difficult to appropriately control the rotational speed, the amount of rinse for the photoresist film, the acceleration and the annealing step prior to the exposure when carrying out the coating process, resulting in obstructing the high integration of devices.

SUMMARY OF THE INVENTION

It is a principal object of the present invention to provide a method for detecting microscopic differences in the thickness of a photoresist film coated on a wafer through naked eyes which avoids the aforementioned problems associated with prior art techniques.

It is another object of the present invention to provide a method for detecting microscopic differences in thickness of a photoresist film coated on a wafer, which is capable of accurately controlling the critical dimension of the photoresist film patterns even in devices of 256 M DRAM or more.

It is a further object of the present invention to provide a method for detecting microscopic differences in the thickness of a photoresist film coated on a wafer, which allows the yield to be analyzed with accuracy.

In accordance with the present invention, the above objects could be accomplished by providing a method for detecting microscopic differences in the thickness of a photoresist film coated on a wafer, comprising the steps of: subjecting the photoresist film to thermal treatment at a low temperature, to make some low-molecular weight compounds or solvent molecules to remain within the photoresist film; forming a special material layer over the photoresist film within a certain thickness; and executing high-temperature thermal treatment, to gush up the remaining low-molecular weight compounds or solvent molecules from the photoresist film through relative thin parts of the special material layer.

BRIEF DESCRIPTION OF THE DRAWINGS

The above object and other advantages of the present invention will become more apparent by describing in detail the preferred embodiments of the present invention with reference to the attached drawings in which.

DETAILED DESCRIPTION OF THE INVENTION

The application of the preferred embodiments of the present invention is best understood with reference to the accompanying drawings.

Figure 2:
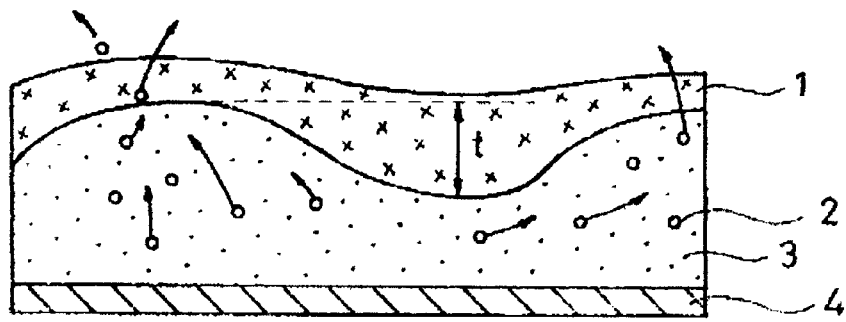
FIG. 2 is a schematic cross sectional view illustrating a process for detecting microscopic differences in the thickness of a photoresist film coated on a wafer, according to the present invention.

With reference to FIG. 2, there is illustrated a process for detecting microscopic differences in the thickness of a photoresist film coated on a wafer. As shown in this figure, a photoresist film 3 is formed on a wafer 4 and then subjected to thermal treatment at low temperatures to make some of low-molecular weight compounds or solvent molecules 2 remain within the photoresist film 3. Thereafter, a special material layer 1, which is different from the photoresist film 3 in component and property, is formed thinly on the treated photoresist film 3. Finally, a thermal treatment at high temperatures allows the low-molecular weight compounds of solvent molecules 2 to gush up in the relative thin parts of the special material layer 1 formed on the photoresist film 3.

The special material layer 1 is about 500 Angstrom or less thick and is formed with a spin-on-glass (SOG) coating or an oxide layer. The latter is formed by a plasma enhanced chemical vapor deposition (PECVD) process. While the low temperature thermal treatment is carried out at a temperature of 150 to 300° C., the high-temperature thermal treatment is at a temperature of 200 to 500° C.

Figure 1:
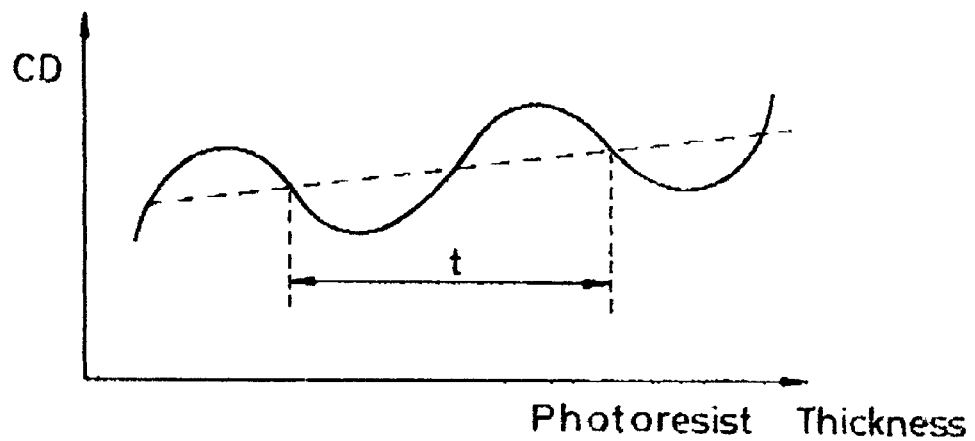
FIG. 1 is a graph showing the periodic change of CD with respect to the thickness of a photoresist film coated on a wafer.

Upon executing the high-temperature thermal process, the low molecular weight compounds or solvent molecules 2 remaining within the photoresist film 3 escape from the photoresist film 3 through the thin parts of the special layer 1 or burst them. In FIG. 1, reference character "t" is a thickness difference of the photoresist film 3, meaning the step level thereof. Accordingly, the special material layer on a low step level is thicker than on a high step level and thus, little defects are shown after the high-temperature thermal treatment.

Figure 3:
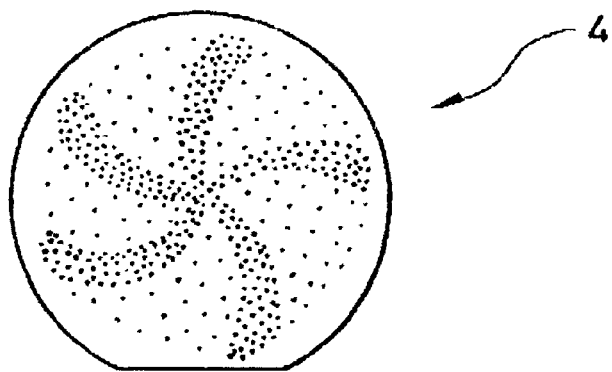
FIG. 3 is a top view showing nonuniformity of the thickness of the photoresist film visibly, according to the present invention.

FIG. 3 is a top view showing defects which are gushed up owing to the difference in thickness of the photoresist film 3 coated on the wafer 4, wherein more densely dotted parts indicate more defects which are generated upon the high-temperature thermal treatment, traceable to relative thin special material layer formed on relative high parts of the photoresist film 3.

As described hereinbefore, the defects generated on coating of a photoresist film can be detected by forming a special material layer subsequent to a low-temperature treatment of the photoresist film and gushing up the defects through thin parts of the photoresist film, or by carrying out the coating step of the special material layer and the low-temperature treatment for 2 to 3 seconds simultaneously.

In accordance with the present invention suggested, coating defectives attributable to microscopic differences in the thickness of a photoresist film can be readily detected, which allows CD to be accurately controlled in devices of 256 M DRAM or more. So, the detecting and monitoring of the process defectives can be achieved, leading to accurate and easy yield analysis.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. A method for detecting microscopic differences in the thickness of a photoresist film coated on a wafer, comprising the steps of:

coating the photoresist film on the wafer;

subjecting the photoresist film to a thermal treatment at a low temperature, to make some solvent molecules remain within the photoresist film;

forming an oxide layer or spin-on-glass layer with 500 Angstrom or less in thickness over the photoresist film;

executing a high-temperature thermal treatment, to gush up the remaining solvent molecules from the photoresist film through relative thin parts of the oxide layer or the spin-on-glass layer; and detecting microscopic differences in the penetration of the oxide layer or the spin-on-glass layer by the solvent molecules in the photoresist film by determining where any solvent molecules have gushed up through the spin-on-glass layer or oxide layer thereby indicating a difference in the thickness of the photoresist film.

2. A method in accordance with claim 1, wherein the oxide is a plasma enhanced chemical vapor deposition oxide layer.

3. A method in accordance with claim 1, wherein the high-temperature thermal treatment is carried out at a temperature of about 200 to about 500° C.

4. A method in accordance with claim 1, wherein the forming step is carried out for 2 to 3 seconds during the low-temperature thermal treatment.

5. A method for detecting microscopic differences in the thickness of a photoresist film coated on a wafer, comprising the steps of:

coating the photoresist film on the wafer;

subjecting the photoresist film to thermal treatment at 150 to approximately 300 degrees Celsius, to make some solvent molecules remain within the photoresist film, forming an oxide layer or a spin-on-glass layer with 500 Angstrom or less in thickness over the photoresist film;

executing thermal treatment at 200–500 degrees Celsius, to gush up the remaining solvent molecules from the photoresist film through relative thin parts of the oxide layer or the spin-on glass layer; and detecting microscopic differences in the penetration of the oxide layer or the spin-on-glass layer by the solvent molecules in the photoresist film by determining where any solvent molecules have gushed up through the spin-on-glass layer or oxide layer thereby indicating a difference in thickness in the photoresist film.

6. A method in accordance with claim 2, wherein the oxide is a plasma enhanced chemical vapor deposition oxide layer.

7. A method in accordance with claim 2, wherein the forming step is carried out for 2 to 3 seconds during the low-temperature thermal treatment.

8. A method for detecting microscopic differences in the thickness of a photoresist film coated on a wafer, comprising the steps of:

coating the photoresist film on the wafer;

subjecting the photoresist film to a thermal treatment at a low temperature, to make some solvent molecules remain within the photoresist film;

forming a spin-on-glass layer with 500 Angstrom or less in thickness over the photoresist film;

executing a high-temperature thermal treatment, to gush up the remaining solvent molecules from the photoresist film through relative thin parts of the spin-on-glass layer; and detecting microscopic differences in the penetration of the spin-on-glass layer by the solvent molecules in the photoresist film by determining where any solvent molecules have gushed up through the spin-on-glass layer thereby indicating a difference in the thickness of the photoresist film.

* * * * *